(12) United States Patent
Corvari et al.

(10) Patent No.: US 6,333,361 B1
(45) Date of Patent: Dec. 25, 2001

(54) PHARMACEUTICAL COMPOSITION CONTAINING ZAFIRLUKAST

(75) Inventors: Susan Jane Corvari, Nashua, NH (US); Karen Beth Main; Bharvnish Vinod Parikh, both of Wilmington, DE (US)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/554,193

(22) PCT Filed: Nov. 10, 1998

(86) PCT No.: PCT/GB98/03371

§ 371 Date: Jul. 11, 2000

§ 102(e) Date: Jul. 11, 2000

(87) PCT Pub. No.: WO99/25338

PCT Pub. Date: May 27, 1999

(30) Foreign Application Priority Data

Nov. 14, 1997 (GB) .................................... 9723985

(51) Int. Cl.[7] ........................ A61K 47/32; A61K 31/405; A61K 9/14; A61K 9/20

(52) U.S. Cl. ........................ 514/772.5; 514/415; 424/486; 424/488; 424/464

(58) Field of Search .................................. 514/415, 772.5; 424/486, 488, 464

(56) References Cited

U.S. PATENT DOCUMENTS 5,482,963 * 1/1996 Holohan et al. ..................... 514/415

FOREIGN PATENT DOCUMENTS

| 0 199 543 | 10/1986 | (EP) . |
|---|---|---|
| 0 490 648 | 6/1992 | (EP) . |
| 0490 649 | 6/1992 | (EP) . |
| WO97/28797 | 8/1997 | (WO) . |
| WO98/41193 | 9/1998 | (WO) . |

* cited by examiner

Primary Examiner—Thurman K. Page
Assistant Examiner—Blessing Fubara
(74) Attorney, Agent, or Firm—Pillsbury Winthrop LLP

(57) ABSTRACT

Pharmaceutical compositions of 4-(5-cyclopentyloxycarbonylamino-1-methylindol-3-ylmethyl)-3-methoxy-N-o-tolylsulfonylbenzamide and a gelling agent, in particular hydroxypropylmethylcellulose, are described for treating asthma and related diseases. Processes for the preparation of the compositions are described.

8 Claims, No Drawings

PHARMACEUTICAL COMPOSITION CONTAINING ZAFIRLUKAST

This application is the national phase of international application PCT/GB98/03371 filed Nov. 10, 1998 which designated the U.S.

The present invention relates to a pharmaceutical composition and more particularly to a pharmaceutical composition comprising 4-(5-cyclopentyloxycarbonylamino-1-methylindol-3-yl-methyl)-3-methoxy-N-o-tolylsulfonylbenzamide (zafirlukast) or a pharmaceutically acceptable salt thereof and a gelling agent.

It is desirable in the treatment of a number of diseases, both therapeutically and prophylactically, to provide the active pharmaceutical ingredient in a form that provides a modified release profile. Such modified release profiles may, in certain circumstances, include controlled release, extended release or sustained release profiles. The modified release formulation provides an alternative dosage form and/or regime which adds to the physician's armoury. Preferably the modified release provides a generally uniform and constant rate of release over an extended period of time which achieves a stable and desired blood (plasma) level of the active ingredient preferably without the need for frequent administration of the medicament.

Accordingly, a need exists for modified release pharmaceutical compositions of medicaments such as, 4-(5-cyclopentyloxycarbonylamino-1-methylindol-3-yl-methyl)-3-methoxy-N-o-tolylsulfonylbenzamide or a pharmaceutically acceptable salt thereof, which provide alternative release profiles and in particular alternative release profiles which achieve more constant blood (plasma) levels throughout the day.

U.S. Pat. No. 4,859,692 discloses formulations which comprise a leukotriene antagonist and croscarmellose sodium (Example 128(i)) or polyvinylpyrrolidone (Example 128 (ii)). U.S. Pat. No. 5,294,636 discloses a formulation which comprises form X of N-[4-[5-(cyclopentyloxycarbonyl)-amino-1-methylindol-3-yl-methyl]-3-methoxybenzoyl]-2-methylbenzenesulphonamide, polyvinylpyrrolidone and croscarmellose sodium (Example 4). U.S. Pat. No. 5,319,097 discloses formulations which comprise form A of N-[4-[5-(cyclopentyloxycarbonyl)-amino-1-methylindol-3-yl-methyl]-3-methoxybenzoyl]-2-methylbenzenesulphonamide, croscarmellose sodium and/or polyvinylpyrrolidone (Examples 3, 5 and comparison Example 3). While it is noted that croscarmellose sodium and polyvinylpyrrolidone can, under certain circumstances, act as gelling agents, the above-described formulations would not provide for formulations with modified release properties as the croscarmellose sodium and polyvinylpyrrolidone are not taught as being present in sufficient enough quantities.

According to the present invention there is provided a modified release pharmaceutical composition comprising a gelling agent, preferably hydroxypropyl methylcellulose, and 4-(5-cyclopentyloxycarbonylamino-1-methylindol-3-yl-methyl)-3-methoxy-N-o-tolylsulfonylbenzamide, or a pharmaceutically acceptable salt thereof. Preferably, the pharmaceutical composition comprises a hydrophilic matrix comprising a gelling agent, preferably hydroxypropyl methylcellulose, and 4-(5-cyclopentyloxy-carbonylamino-1-methylindol-3-yl-methyl)-3-methoxy-N-o-tolylsulfonylbenzamide, or a pharmaceutically acceptable salt thereof, optionally together with one or more pharmaceutically acceptable excipients.

The term gelling agent as used herein means any substance, particularly a hydrophilic substance, which forms a gel when in contact with water and thus includes such substances as hydroxypropyl methylcellulose, hydroxypropylcellulose, hydroxymethylcellulose, hydroxyethylcellulose, hydroxypropyl ethylcellulose, methylcellulose, ethylcellulose, carboxyethylcellulose, carboxymethyl hydroxyethylcellulose, carbomer, sodium carboxymethylcellulose, polyvinylpyrrolidone, or mixtures thereof. The gelling agent is preferably hydroxypropyl methylcellulose.

The gelling agent, for example hydroxypropyl methylcellulose, is preferably present in an amount which is sufficient to provide a matrix. This matrix formulation is believed to provide a modified release profile. The gelling agent is conveniently present in about 5 to 50% (by weight), more conveniently about 5 to 45%, most conveniently about 5 to 40%, preferably about 9 to 40%, more preferably about 14 to 40%, most preferably about 20 to 40% and in particular about 25 to 40%.

The hydroxypropyl methylcellulose may contain more than one grade of polymer and is commercially available under several trademarks, e.g. METHOCEL® E, F, J and K from the Dow Chemical Company, U.S.A. and METOLOSE™ SH from Shin-Etsu, Ltd., Japan. The various grades available under a given trademark represent differences in methoxy and hydroxypropoxy content as well as in viscosity. The methoxy content ranges from 16.5 to 30% by weight, the hydroxypropoxy content ranges from 4 to 32% by weight and the viscosities of a 2% aqueous solution at 20° C. range from 3 cps to 100,000 cps. For example, the hydroxypropyl methylcellulose preferably comprises (a) a polymer with a viscosity of about 40 to 60 cps (in particular about 50 cps), a methoxy content of about 28 to 30% by weight and a hydroxypropoxy content of from about 7 to less than 9% by weight; or (b) a polymer with a viscosity of about 3,500 to 5,600 cps (in particular about 4,000 cps), a methoxy content of about 28 to 30% by weight and a hydroxypropoxy content of about 7 to 12% by weight; or (c) a polymer with a viscosity of about 80 to 120 cps (in particular about 100 cps), a methoxy content of about 19 to 24% by weight and a hydroxypropoxy content of from about 7 to less than 9% by weight; or (d) a polymer with a viscosity of about 3500 to 5600 cps (in particular about 4,000 cps), a methoxy content of about 19 to 24% by weight and a hydroxypropoxy content of about 7 to 12% by weight, or mixtures thereof. More preferably, the hydroxypropyl methylcellulose is selected from the group consisting of (a)–(d) or mixtures thereof as described above and in particular from the group consisting of (a), (c) and (d) or mixtures thereof as described above, with the proviso that if the pharmaceutical composition contains a hydroxypropyl methylcellulose described under (d) above the total amount of hydroxypropyl methylcellulose present in the pharmaceutical composition must be greater than 25.8% by weight.

The compound, 4-(5-cyclopentyloxycarbonylamino-1-methylindol-3-yl-methyl)-3-methoxy-N-o-tolylsulfonylbenzamide (see Formula I below), its various physical forms and its pharmaceutically acceptable salts exhibit useful leukotriene antagonist activity. Thus, they antagonize the actions of one or more of

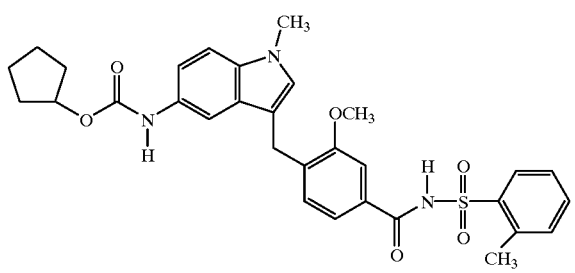

I the arachidonic acid metabolites known as leukotrienes, for example, $C_4$, $D_4$, and/or $E_4$, which are known to be powerful spasmogens (particularly in the lung), to increase vascular permeability and have been implicated in the pathogenesis of asthma and inflammation (see J. L. Marx, *Science*, 1982, 215 1380–1383) as well as endotoxic shock (see J. A. Cook, et al., *J. Pharmacol. Exp. Ther.*, 1985, 235, 470) and traumatic shock (see C. Denzlinger et al., *Science*, 1985. 230, 330). The compounds are thus useful in the treatment of diseases in which leukotrienes are implicated and in which antagonism of their action is desired. Such diseases include for example, allergic pulmonary disorders such as asthma, hay fever and allergic rhinitis and certain inflammatory diseases such as bronchitis, ectopic and atopic eczema, and psoriasis as well as vasospastic cardiovascular disease and endotoxic and traumatic shock conditions. The compounds are particularly useful in the treatment of asthma.

The preparation, physical properties and beneficial pharmacological properties of 4-(5-cyclopentyloxycarbonylamino-1-methylindol-3-yl-methyl)-3-methoxy-N-o-tolylsulfonylbenzamide, its various physical forms and its pharmaceutically acceptable salts are described in European Patents EP 199,543, 490,649 and 490,648 as well as in corresponding U.S. Pat. Nos. 4,859, 692, 5,294,636 and 5,319,097, the entire contents of which are herein incorporated by reference. The compositions of the present invention may include any physical form of the compound preferably the compound exists in the amorphous physical form.

In particular the 4-(5-cyclopentyloxycarbonylamino-1-methylindol-3-yl-methyl)-3-methoxy-N-o-tolylsulfonylbenzamide, or pharmaceutically acceptable salt thereof is present in about 10 to 90% by weight, preferably about 10 to 80% by weight, more preferably about to 65% by weight, most preferably about 10 to 40% by weight and especially about 10 to 32% by weight.

The pharmaceutical composition will, in general, contain one or more excipients. Such excipients will include diluents such as lactose, microcrystalline cellulose, dextrose, mannitol, sucrose, sorbitol, gelatin, acacia, dicalcium phosphate, tricalcium phosphate, monocalcium phosphate, sodium phosphate, sodium carbonate and the like, preferably lactose and microcrystalline cellulose; lubricants such as stearic acid, zinc, calcium or magnesium stearate and the like, preferably magnesium stearate; binders such as sucrose, polyethylene glycol, povidone (polyvinylpyrrolidone), corn or maize starch, pregelatinized starch and the like, preferably povidone (polyvinylpyrrolidone); colorants such as ferric oxides, FD & C dyes, lakes and the like, and flavoring agents. The excipient(s) will, in general, be present in about 10 to 90% by weight, preferably about 20 to 85% by weight, more preferably about 25 to 85% by weight, and most preferably about 28 to 81% by weight. The pharmaceutical composition preferably may contain one or more pharmaceutically acceptable excipients selected from the group consisting of microcrystalline cellulose, lactose, magnesium stearate and povidone. In particular, the pharmaceutical composition may contain one or more of (a) microcrystalline cellulose, preferably in the amount of about 10 to 60% by weight, (b) lactose, preferably in the amount of about 10 to 40% by weight, (c) magnesium stearate, preferably in the amount of about 0.5 to 3% by weight, and (d) about 1 to 15% by weight, preferably about 2 to 6% by weight of povidone (polyvinylpyrrolidone).

The pharmaceutical compositions of particular interest include those described in the accompanying Examples and so compositions substantially as defined in the accompanying Examples are provided as a further feature of the present invention.

As mentioned above, the compound 4-(5-cyclopentyloxycarbonyl-amino-1-methylindol-3-yl-methyl)-3-methoxy-N-o-tolylsulfonylbenzamide, and its pharmaceutically acceptable salts, exhibit useful leukotriene antagonist activity and may be used in the treatment of those diseases in which leukotrienes are implicated and in which antagonism of their action is desired. Thus, the present invention also provides a method of antagonizing one or more of the actions of leukotrienes in a mammal, such as man, which comprises administering to said mammal an effective amount of a pharmaceutical composition of the present invention.

The present invention also provides a method for the treatment of allergic pulmonary disorders, inflammatory diseases, vasospastic cardiovascular disease, endotoxic compositions and traumatic shock conditions in a mammal which comprises administering to said mammal an effective amount of a pharmaceutical composition of the present invention.

The present invention also provides a method for the treatment of asthma in a mammal which comprises administering to said mammal an effective amount of a pharmaceutical composition of the present invention.

The pharmaceutical compositions of the present invention can be prepared for pharmaceutical use by conventional technology well known to those skilled in the art such as wet granulation, direct compression dry compaction (slugging) and the like. Thus, for example, the active ingredient 4-(5-cyclopentyloxycarbonylamino-1-methylindol-3-yl-methyl)-3-methoxy-N-o-tolylsulfonylbenzamide, or a pharmaceutically acceptable salt thereof, a gelling agent, preferably hydroxypropyl methylcellulose, and other excipients are mixed together to form the compositions of the present invention. Preferably the active ingredient 4-(5-cyclopentyloxycarbonylamino-1-methylindol-3-yl-methyl)-3-methoxy-N-o-tolylsulfonylbenzamide, or a pharmaceutically acceptable salt thereof, a gelling agent, preferably hydroxypropyl methylcellulose, and other excipients are mixed together to form a mixture suitable for compressing into tablets, which mixture is then compressed to form tablets or is filled into capsules or sachets.

The mixing process is preferably carried out by mixing the components, wet granulating the mixed components, drying the mixture, milling the dried mixture, blending the mixture with a lubricant such as magnesium stearate and compressing the blended mixture to form tablets or filling the blended mixture into capsules or sachets.

A preferred process for preparing the pharmaceutical compositions of the invention comprises the following steps:

(a) mixing 4-(5-cyclopentyloxycarbonylamino-1-methylindol-3-yl-methyl)-3-methoxy-N-o-tolylsulfonylbenzamide, or a pharmaceutically acceptable salt thereof, a gelling agent, preferably hydroxypropyl methylcellulose, and other excipients;

(b) wet granulating the mixed components;

(c) drying the mixture;

(d) milling the dried mixture;

(e) blending the mixture with a lubricant such as magnesium stearate; and (f) compressing the blended mixture to form tablets.

The dosage forms may be coated with one or more coatings as is well known in the art such as, for example, shellac, zein, hydroxypropyl cellulose, hydroxypropyl methylcellulose, ethyl cellulose, polymethacrylates, polyvinyl acetate phthalate, cellulose acetate phthalate, triacetin, dibutyl sebacate, a mixture of polyethylene glycol, titanium dioxide and hydroxypropyl methylcellulose, and the like.

The modified release properties of the pharmaceutical compositions of the present invention may be demonstrated by monitoring the dissolution of the active ingredient. The dissolution of the active ingredient may be monitored using standard procedures well known to those skilled in the art (e.g. the dissolution test procedures, such as the Rotating Basket Method (Apparatus I) or Paddle Method (Apparatus II), disclosed in the U.S. Pharmacopeia (USP)). Such procedures include those in which the formulation is immersed in an aqueous medium such as water, 1% sodium dodecyl sulfate or hydrochloric acid and aliquots of the medium are withdrawn at various time points over a period of 24 hours. The aliquots are analyzed using high pressure liquid chromatography (HPLC) with UV detection to determine the concentration of dissolved active ingredient using standard methodology. In a particular example a tablet is immersed in about 1000 mL of 1% sodium dodecyl sulfate and the dissolution profile determined according to the Paddle method.

The dissolution profile of the pharmaceutical compositions of Examples 1–4 are shown in Table A and the dissolution profile of the pharmaceutical compositions of examples 5–11 are shown in Table B.

TABLE A

| | Percent Released in 1% Sodium Dodecyl Sulfate | | | |
|---|---|---|---|---|
| Time (hours) | Example 1 | Example 2 | Example 3 | Example 4 |
| 1 | 21.6 | — | 18.6 | 21.8 |
| 2 | 33.8 | 36.4 | 33.20 | 38.45 |
| 4 | 66.9 | 64.6 | 58.55 | 67.40 |
| 6 | 94.4 | 87.6 | 80.35 | 87.45 |
| 8 | — | 94.7 | 92.30 | 92.85 |
| 10 | — | 95.0 | — | — |
| 12 | — | 94.0 | — | — |
| 15 | — | 94.2 | — | — |
| 18 | — | 94.4 | — | — |
| 21 | — | 94.5 | — | — |
| 24 | 99.9 | 95.0 | 95.05 | 93.0 |

TABLE B

| | Percent Released in 1% Sodium Dodecyl Sulfate | | | | | | |
|---|---|---|---|---|---|---|---|
| Time (hours) | Example 5 | Example 6 | Example 7 | Example 8 | Example 9 | Example 10 | Example 11 |
| 2 | 26.8 | 25.9 | 17.2 | 17.4 | 26.1 | 23.1 | 17.4 |
| 4 | 46.1 | 49.2 | 34.2 | 51.1 | 50.4 | 45.5 | 35.0 |
| 6 | 59.7 | 68.9 | 49.4 | 74.2 | 71.0 | 64.8 | 51.0 |
| 8 | 69.8 | 83.1 | 62.5 | 84.0 | 87.8 | 81.5 | 64.8 |
| 10 | 77.2 | 92.2 | 73.5 | 87.5 | 95.2 | 94.0 | 77.1 |
| 12 | 79.2 | 93.0 | 81.2 | 84.9 | 95.7 | 95.1 | 83.9 |
| 15 | 76.5 | 91.2 | 83.6 | 82.9 | 94.4 | 94.5 | 85.1 |
| 18 | 75.0 | 88.9 | — | — | — | — | — |
| 21 | 74.2 | 87.3 | — | — | — | — | — |
| 24 | 72.4 | 86.8 | 77.9 | 79.3 | 89.3 | 90.3 | 82.5 |

The pharmaceutical compositions of the present invention are generally administered to patients which include, but are not limited to, mammals, such as, for example, man.

It will also be apparent to those skilled in the art that the pharmaceutical compositions of the present invention can be co-administered with other therapeutic or prophylactic agents and/or medicaments that are not medically incompatible therewith.

The pharmaceutical compositions of the present invention do not, in general, show any indication of overt toxicity in laboratory test animals at several multiples of the minimum effective dose of the active ingredient.

The percentage of active component in the compositions of the present invention may be varied so that a suitable dosage is obtained. The dosage administered to a particular patient is variable depending upon the clinician's judgement using as criteria: the route of administration, the duration of treatment, the size, age, and physical condition of the patient, the severity of the condition, the potency of the active component and the patient's response thereto. An effective dosage amount of the active component can thus readily be determined by the clinician after a consideration of all criteria and using his best judgement on the patient's behalf. In general, a compound of the instant invention is administered to patients at a dose in the range of about 0.01 to about 40 mg/kg body weight. Preferably, the compound of the present invention is administered in about a 10, 20, 40, 80, or 160 mg strength.

The pharmaceutical compositions of the present invention will, in general, be in the form of a unit dosage form, and, in particular, will be in the form of a tablet.

The invention is further illustrated by the following non-limiting Examples in which temperatures are expressed in degrees Celsius. Viscosities referred to herein are measured at 2% concentration in water at 20° C.

The compound 4-(5-cyclopentyloxycarbonylamino-1-methylindol-3-yl-methyl)-3-methoxy-N-o-tolylsulfonylbenzamide, its various physical forms and its pharmaceutically acceptable salts, may be prepared as described in European Patents EP 199,543, 490,649 and 490,648 as well as in corresponding U.S. Pat. Nos. 4,859,692, 5,294,636 and 5,319,097, the entire contents of which are herein incorporated by reference.

EXAMPLE 1

The following process was used to prepare tablets having the composition defined in Table 1.

4-(5-Cyclopentyloxycarbonylamino-1-methylindol-3-yl-methyl)-3-methoxy-N-o-tolylsulfonylbenzamide (40.00 mg), lactose (84.55 mg), microcrystalline cellulose (84.55 mg) and METHOCEL® K100LV Premium CR (36.90 mg) were blended in a high shear mixer at high speed for approximately 2 minutes.

The mixture was wet granulated in a high shear mixer at low speed using purified water. The wet mass was dried in a fluidized bed drier at about 65° C. until the loss on drying was less than about 2% as measured by a moisture balance.

The dried granulation was milled using a hammer type or similar mill operating at fast speed, knives forward with suitable screen (e.g. 20 to 40 mesh).

Magnesium stearate was passed through an appropriate screen (e.g. 20 to 40 mesh).

The dry granulated material was blended for approximately 2 minutes in a conventional blender (for example, Patterson-Kelley Twin Shell) with the screened magnesium stearate and with microcrystalline cellulose (150.00 mg).

The blended mixture was compressed into tablets using a conventional rotary tablet press (for example, Kilian LX-21).

TABLE 1

|  | mg/Tablet | % of Tablet |
| --- | --- | --- |
| Active ingredient (a) | 40.00 | 10.0 |
| Lactose NF | 84.55 | 21.14 |
| Microcrystalline Cellulose NF | 84.55 | 21.14 |
| METHOCEL ® K100LV Premium CR (b) | 36.90 | 9.22 |
| Purified water (c) | q.s. | — |

TABLE 1-continued

|  | mg/Tablet | % of Tablet |
| --- | --- | --- |
| Magnesium stearate NF | 4.00 | 1.0 |
| Microcrystalline Cellulose MF | 150.00 | 37.5 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K100LV Premium CR is hydroxypropyl methylcellulose with a viscosity of 80–120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in this example had a viscosity of 107 cps, a methoxy content of 22.8% by weight and a hydroxypropoxy content 10.2% by weight.
(c) Added but not retained.

EXAMPLE 2

The following process was used to prepare tablets having the composition defined in Table 2.

4-(5-Cyclopentyloxycarbonylamino-1-methylindol-3-yl-methyl)-3-methoxy-N-o-tolylsulfonylbenzamide (40.00 mg), lactose (84.55 mg), microcrystalline cellulose (84.55 mg) and METHOCEL® K100LV Premium CR (36.90 mg) were blended in a high shear mixer at high speed for approximately 2 minutes.

The mixture was wet granulated in a high shear mixer at low speed using purified water. The wet mass was dried in a fluidized bed drier at about 65° C. until the loss on drying was less than about 2% as measured by a moisture balance.

The dried granulation was milled using a hammer type or similar mill operating at fast speed. knives forward with suitable screen (e.g. 20 to 40 mesh).

Magnesium stearate was passed through an appropriate screen (e.g. 20 to 40 mesh).

The dry granulated material was blended for approximately 2 minutes in a conventional blender (for example, Patterson-Kelley Twin Shell) with the screened magnesium stearate.

The blended mixture was compressed into tablets using a conventional rotary tablet press (for example, Kilian LX-21).

TABLE 2

|  | mg\Tablet | % of Tablet |
| --- | --- | --- |
| Active ingredient (a) | 40.00 | 16.0 |
| Lactose NF | 84.55 | 33.8 |
| Microcrystalline Cellulose NF | 84.55 | 33.8 |
| METHOCEL ® K100LV Premium CR (b) | 36.90 | 14.8 |
| Purified water (c) | q.s. | — |
| Magnesium stearate NF | 4.00 | 1.6 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K100LV Premium CR is hydroxypropyl methylcellulose with a viscosity of 80–120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in this example had a viscosity of 104 cps, a methoxy content of 21.7% by weight and a hydroxypropoxy content 8.7% by weight.
(c) Added but not retained.

Following a procedure similar to that described in Example 2, tablets of the following compositions shown in Tables 3 to 7 were prepared.

TABLE 3

|  | Example 3 | | Example 4 | |
| --- | --- | --- | --- | --- |
|  | mg\Tablet | % of Tablet | mg\Tablet | % of Tablet |
| Active ingredient (a) | 40.00 | 16.00 | 40.00 | 16.00 |
| Lactose NF | 84.55 | 33.8 | 90.70 | 36.3 |
| Microcrystalline Cellulose NF | 84.55 | 33.8 | 90.70 | 36.3 |
| METHOCEL ® K100LV Premium CR (b) | 18.45 | 7.4 | 24.60 | 9.8 |
| METHOCEL ® E50LV Premium CR (c) | 18.45 | 7.4 | — | — |
| Purified water (d) | q.s. | — | q.s. | — |
| Magnesium stearate NF | 4.00 | 1.6 | 4.00 | 1.6 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in these examples had a viscosity of 107 cps, a methoxy content of 22.8% by weight and a hydroxypropoxy content 10.2% by weight.
(c) METHOCEL ® E50LV Premium CR is hydroxypropyl methylcellulose with a viscosity of 40 to 60 cps, a methoxy content of 28 to 30% by weight and a hydroxypropoxy content of 7 to 12% by weight which may be obtained from The Dow Chemical Company, Michigan, USA. This product meets the specifications for HPMC 2910 USP. Note that the particular METHOCEL ® E50LV Premium CR utilized in these examples had a viscosity of 44 cps, a methoxy content of 29.3% by weight and a hydroxypropoxy content 9.1% by weight.
(d) Added but not retained.

TABLE 4

|  | Example 5 | | Example 6 | |
| --- | --- | --- | --- | --- |
|  | mg/tablet | % of Tablet | mg/Tablet | % of Tablet |
| Active ingredient (a) | 80.00 | 32.00 | 80.00 | 32.0 |
| Lactose NF | 65.00 | 26.00 | 52.00 | 20.8 |
| Microcrystalline Cellulose NF | 65.00 | 26.00 | 53.00 | 21.2 |
| METHOCEL ® K100LV Premium CR (b) | 37.50 | 15.00 | 62.50 | 25.0 |
| METHOCEL ® K4M Premium CR (c) | — | — | — | — |
| Purified water (d) | q.s. | — | q.s. | — |
| Magnesium stearate NF | 2.50 | 1.00 | 2.50 | 1.00 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in these examples had a viscosity of 90 cps, a methoxy content of 22.7% by weight and a hydroxypropoxy content 8.5% by weight for examples 5 and 6 and a viscosity of 109 cps, a methoxy content of 22.6% by weight and a hydroxypropoxy content of 8.6% by weight for examples 8–11.
(c) METHOCEL ® K4M Premium CR is hydroxypropyl methylcellulose with a viscosity of 3,500 to 5,600 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K4M Premium CR utilized in these examples had a viscosity of 4105 cps, a methoxy content of 22.3% by weight and a hydroxypropoxy content 9.7% by weight.
(d) Added but not retained.

TABLE 5

|  | Example 7 | | Example 8 | |
| --- | --- | --- | --- | --- |
|  | mg/tablet | % of Tablet | mg/Tablet | % of Tablet |
| Active ingredient (a) | 80.00 | 32.00 | 80.00 | 32.00 |
| Lactose NF | 46.25 | 18.5 | 46.25 | 18.50 |
| Microcrystalline Cellulose NF | 46.25 | 18.5 | 46.25 | 18.50 |
| METHOCEL ® K100LV Premium CR (b) | — | — | 37.50 | 15.00 |
| METHOCEL ® K4M Premium CR (c) | 75.00 | 30.00 | 37.50 | 15.00 |
| Purified water (d) | q.s. | — | q.s. | — |
| Magnesium stearate NF | 2.50 | 1.00 | 2.50 | 1.00 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in these examples had a viscosity of 90 cps, a methoxy content of 22.7% by weight and a hydroxypropoxy content 8.5% by weight for examples 5 and 6 and a viscosity of 109 cps, a methoxy content of 22.6% by weight and a hydroxypropoxy content of 8.6% by weight for examples 8–11.
(c) METHOCEL ® K4M Premium CR is hydroxypropyl methylcellulose with a viscosity of 3,500 to 5,600 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K4M Premium CR utilized in these examples had a viscosity of 4105 cps, a methoxy content of 22.3% by weight and a hydroxypropoxy content 9.7% by weight.
(d) Added but not retained.

TABLE 6

|  | Example 9 | | Example 10 | |
| --- | --- | --- | --- | --- |
|  | mg/tablet | % of Tablet | mg/Tablet | % of Tablet |
| Active ingredient (a) | 80.00 | 32.00 | 80.00 | 32.00 |
| Lactose NF | 46.25 | 18.50 | 40.00 | 16.00 |
| Microcrystalline Cellulose NF | 46.25 | 18.50 | 40.00 | 16.00 |
| METHOCEL ® K100LV Premium CR (b) | 62.50 | 25.00 | 62.50 | 25.00 |
| METHOCEL ® K4M Premium CR (c) | 12.50 | 5.00 | 25.00 | 10.00 |
| Purified water (d) | q.s. | — | q.s. | — |
| Magnesium stearate NF | 2.50 |  | 2.50 | 1.00 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in these examples had a viscosity of 90 cps, a methoxy content of 22.7% by weight and a hydroxypropoxy content 8.5% by weight for examples 5 and

TABLE 6-continued 6 and a viscosity of 109 cps, a methoxy content of 22.6% by weight and a hydroxypropoxy content of 8.6% by weight for examples 8–11.
(c) METHOCEL ® K4M Premium CR is hydroxypropyl methylcellulose with a viscosity of 3,500 to 5,600 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K4M Premium CR utilized in these examples had a viscosity of 4105 cps, a methoxy content of 22.3% by weight and a hydroxypropoxy content 9.7% by weight.
(d) Added but not retained.

TABLE 7

|  | Example 11 | |
| --- | --- | --- |
|  | % of Tablet | mg/tablet |
| Active ingredient (a) | 80.00 | 32.00 |
| Lactose NF | 33.75 | 13.50 |
| Microcrystalline Cellulose NF | 33.75 | 13.50 |
| METHOCEL ® K100LV Premium CR (b) | 62.50 | 25.00 |
| METHOCEL ® K4M Premium CR (c) | 37.50 | 15.00 |
| Purified water (d) | q.s. | — |
| Magnesium stearate NF | 2.50 | 1.00 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K100LV Premium CR is hydroxypropyl methylcellulose with a viscosity of 80 to 120 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K100LV Premium CR utilized in these examples had a viscosity of 90 cps, a methoxy content of 22.7% by weight and a hydroxypropoxy content 8.5% by weight for examples 5 and 6 and a viscosity of 109 cps, a methoxy content of 22.6% by weight and a hydroxypropoxy content of 8.6% by weight for examples 8–11.
(c) METHOCEL ® K4M Premium CR is hydroxypropyl methylcellulose with a viscosity of 3,500 to 5,600 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K4M Premium CR utilized in these examples had a viscosity of 4105 cps, a methoxy content of 22.3% by weight and a hydroxypropoxy content 9.7% by weight.
(d) Added but not retained.

EXAMPLE 12

The following process was used to prepare tablets having the composition defined in Table 8.

4-(5-Cyclopentyloxycarbonylamino-1-methylindol-3-yl-methyl)-3-methoxy-N-o-tolylsulfonylbenzamide (80.00 mg), lactose (42.50 mg), microcrystalline cellulose (42.50 mg), povidone (7.50 mg) and METHOCEL® K4M Premium CR (75.00 mg) were blended in a high shear mixer at high speed for approximately 2 minutes.

The mixture was wet granulated in a high shear mixer at low speed using purified water. The wet mass was dried in a fluidized bed drier at about 65° C. until the loss on drying was less than about 2% as measured by a moisture balance.

The dried granulation was milled using a hammer type or similar mill operating at fast speed, knives forward with suitable screen (e.g. 20 to 40 mesh).

Magnesium stearate was passed through an appropriate screen (e.g. 20 to 40 mesh).

The dry granulated material was blended for approximately 2 minutes in a conventional blender (for example, Patterson-Kelley Twin Shell) with the screened magnesium stearate.

The blended mixture was compressed into tablets using a conventional rotary tablet press (for example, Kilian LX-21).

TABLE 8

|  | mg\Tablet | % of Tablet |
| --- | --- | --- |
| Active ingredient (a) | 80.00 | 32.00 |
| Lactose NF | 42.50 | 17.00 |
| Microcrystalline Cellulose NF | 42.50 | 17.00 |
| METHOCEL ® K4M Premium CR (b) | 75.00 | 30.00 |
| Povidone USP (c) | 7.50 | 3.00 |
| Purified water (d) | q.s. | — |
| Magnesium stearate NF | 2.50 | 1.00 |

(a) The active ingredient is 4-(5-cyclopentyloxycarbonylamino-1-methylindol-3-yl-methyl)-3-methoxy-N-o-tolylsulfonylbenzamide.
(b) METHOCEL ® K4M Premium CR is hydroxypropyl methylcellulose with a viscosity of 3,500 to 5,600 cps, a methoxy content of 19 to 24% by weight and a hydroxypropoxy content of 7 to 12% by weight which may be obtained from The Dow Chemical Company, Michigan, USA. This product meets the specifications for HPMC 2208 USP. Note that the particular METHOCEL ® K4M Premium CR utilized in these examples had a viscosity of 4105 cps, a methoxy content of 22.3% by weight and a hydroxypropoxy content 9.7% by weight.
(c) This reagent is a polyvinylpyrrolidone polymer having a K-value of 29-32 which may be obtained from ISP Technologies Inc., Wayne, New Jersey, USA, under the trademark PLASDONE ® K-29/32. This product meets the specification for Povidone USP.
(d) Added but not retained.

What is claimed is:

1. A pharmaceutical composition comprising
4-(5-cyclopentyloxycarbonylamino-1-methylindol-3-ylmethyl)-3-methoxy-N-o-tolylsulfonylbenzamide or a pharmaceutically acceptable salt thereof, and, as gelling agent, hydroxypropylmethylcellulose, wherein the hydroxypropylmethylcellulose is selected from the group consisting of:
   a) a hydroxypropylmethylcellulose having a viscosity of about 40 to 60 cps, a methoxy content of about 20 to 30% by weight and a hydroxypropoxy content of from about 7 to less than 9% by weight;
   b) a hydroxypropylmethylcellulose having a viscosity of about 3,500 to 5,600 cps, a methoxy content of about 28 to 30% by weight and a hydroxypropoxy content of about 7 to 12% by weight;
   c) a hydroxypropylmethlylcellulose having a viscosity of about 80 to 120 cps, a methoxy content of about 19 to 24% by weight and a hydroxypropoxy content of from about 7 to less than 9% by weight; and
   d) a hydroxypropylmethylcellulose having a viscosity of about 5,500 to 5,600 cps, a methoxy content of about 19 to 24% by weight and a hydroxypropoxy content of about 7 to 12% by weight, or mixtures thereof.

2. The composition according to claim 1 wherein the hydroxypropylmethlylcellulose is present in about 5 to 50% (by weight).

3. The composition according to claim 2 wherein the hydroxypropylmethylcellulose is present in about 14 to 40% (by weight).

4. The composition according to claim 1 comprising at least one excipient selected from the group consisting of lactose, microcrystalline cellulose, dextrose, mannitol, sucrose, sorbitol, gelatin, acacia, dicalcium phosphate, tricalcium phosphate, monocalcium phosphate, sodium phosphate, sodium cargonate, stearic acid, polyethylene glycol, polyvinylpyrrolidone, corn or maize starch, pregelatinized starch, colorants and flavoring agents.

5. The composition according to claim 4 which comprises one or more of:
   a) 10–60% microcrystalline cellulose;
   b) 10–40% lactose;

c) 0.5–3% magnesium stearate; and d) 1–15% polyvinylpyrrolidone.

6. The composition according to claims 4 or 5 which comprises 2–6% polyvinylpyrrolidone.

7. A process for preparing a pharmaceutical composition comprising 4-(5-cyclopentyloxycarbonylamino-1-methylindol-3-ylmethyl)-3-methoxy-N-o-tolylsulfonylbenzamide or a pharmaceutically acceptable salt thereof, and, as gelling agent, hydroxypropylmethylcellulose, wherein the hydroxypropylmethylcellulose is selected from the group consisting of:

a) a hydroxypropylmethylcellulose having a viscosity of about 50 to 60 cps, a methoxy content of about 20 to 30% by weight and a hydroxypropoxy content of from about 7 to less than 9% by weight;

b) a hydroxypropylmethylcellulose having a viscosity of about 3,500 to 5,600 cps, a methoxy content of about 28 to 30% by weight and a hydroxypropoxy content of about 7 to 12% by weight;

c) a hydroxypropylmethylcellulose having a viscosity of about 80 to 120 cps, a methoxy content of about 19 to 24% by weight and a hydroxypropoxy content of from about 7 to less than 9% by weights; and d) a hydroxypropylmethylcellulose having a viscosity of about 3,500 to 5,600 cps, a methoxy content of about 19 to 24% by weight and a hydroxypropoxy content of about 7 to 12% by weight, or mixtures thereof.

8. A method of antagonising one or more of the actions of leukotrienes in a mammal, which comprises administrating to said mammal an effective amount of a pharmaceutical composition as claimed in claim 1.

* * * * *